(12) United States Patent
Munagavalasa et al.

(10) Patent No.: US 6,482,863 B2
(45) Date of Patent: Nov. 19, 2002

(54) INSECT REPELLANT FORMULATION DELIVERABLE BY PIEZOELECTRIC DEVICE

(75) Inventors: Murthy S. Munagavalasa; Gopal P. Ananth, both of Racine, WI (US); Kevan Gartland, Selborne (GB)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/738,516

(22) Filed: Dec. 15, 2000

(65) Prior Publication Data

US 2002/0147179 A1 Oct. 10, 2002

(51) Int. Cl.$^7$ .................. A01N 31/00; A61K 31/045
(52) U.S. Cl. .................. 514/724; 514/738; 424/405
(58) Field of Search ............. 514/65, 724, 738; 424/405

(56) References Cited

U.S. PATENT DOCUMENTS

| | | |
|---|---|---|
| 3,543,122 A | 11/1970 | Klebanoff et al. |
| 3,615,041 A | 10/1971 | Bischoff |
| 3,649,720 A | 3/1972 | Leber |
| 3,679,667 A | 7/1972 | Fanta |
| 3,709,960 A | 1/1973 | Lutz et al. |
| 3,996,375 A | 12/1976 | Frensch et al. |
| 4,173,651 A | 11/1979 | Muramoto et al. |
| 4,268,460 A | 5/1981 | Boiarski et al. |
| 4,316,914 A | 2/1982 | Coffee et al. |
| 4,381,533 A | 4/1983 | Coffee |
| 4,476,515 A | 10/1984 | Coffee |
| 4,479,609 A | 10/1984 | Maeda et al. |
| RE31,927 E | 6/1985 | Coffee et al. |
| 4,533,082 A | 8/1985 | Maehara et al. |
| 4,628,040 A | 12/1986 | Green et al. |
| 4,656,963 A | 4/1987 | Yonehara et al. |
| 4,702,418 A | 10/1987 | Carter et al. |
| 4,790,479 A | 12/1988 | Matsumoto et al. |
| 5,064,639 A | * 11/1991 | Dohara et al. ............... 424/45 |
| 5,297,734 A | 3/1994 | Toda |
| 5,312,281 A | 5/1994 | Takahashi et al. |
| 5,382,410 A | 1/1995 | Peltier |
| 5,518,179 A | 5/1996 | Humberstone et al. |
| 5,657,926 A | 8/1997 | Toda |
| 5,660,166 A | 8/1997 | Lloyd et al. |
| 5,736,195 A | 4/1998 | Haaland |
| 5,758,637 A | 6/1998 | Ivri et al. |
| 5,823,428 A | 10/1998 | Humberstone et al. |
| 5,935,554 A | 8/1999 | Tomlinson |
| 5,938,117 A | 8/1999 | Ivri |
| 5,945,111 A | 8/1999 | Esser |

FOREIGN PATENT DOCUMENTS

| | | | |
|---|---|---|---|
| EP | 0678337 A1 | | 3/1995 |
| EP | 0762211 A1 | | 8/1996 |
| EP | 0897755 A2 | | 2/1999 |
| GB | 973458 | | 10/1962 |
| GB | 2 073616 | | 4/1981 |
| JP | 09077604 | * | 3/1997 |
| RU | 1007752 | | 3/1983 |

* cited by examiner

*Primary Examiner*—Alton Pryor

(57) ABSTRACT

Homogenous insecticidal compositions are disclosed in which a non-polar insecticide is dissolved in one or more polar solvents. The compositions have very low viscosity and high flash points and are suitable for use with a piezoelectric liquid atomizer.

14 Claims, No Drawings

INSECT REPELLANT FORMULATION DELIVERABLE BY PIEZOELECTRIC DEVICE

BACKGROUND OF THE INVENTION

1. Field of the Invention

The invention is directed to insect repellent formulations which contain polar solvents, have low viscosity, and are deliverable by piezoelectric device.

2. Description of the Related Art

Sprayable insecticidal compositions are known and generally comprise an insecticide and a solvent, in addition to other components. As the common insecticides are non-polar, the most common solvents used for this purpose are themselves non-polar, e.g. hydrocarbon solvents, such as hexane and petroleum solvent blends available under the trade names Shellsol and Isopar, for example.

While hydrocarbon solvents are effective to dissolve most common non-polar insecticides, they tend to have low flash points and to otherwise pose environmental and health risks. Therefore, it is desired to develop sprayable insecticidal compositions which avoid or minimize the use of these solvents. An insecticide formulation deliverable by piezoelectric delivery system which minimizes or avoids the use of non-polar solvents would be an advancement in the art.

Low-flash point solvents typically have high volatility. High volatility results in unintended evaporation of the insecticidal formulation—so-called "latent losses." The problem of latent losses is particularly acute when the formulations are intended for delivery by a piezoelectric device over an extended period of time. For this and other reasons, there is a need in the art for insecticidal formulations using low-volatility solvents which are deliverable by piezoelectric device.

U.S. Pat. No. Re. 31,927 discloses electrostatically sprayable insecticidal formulations. High-boiling, high flash point hydrocarbon solvents, such as Isopar L are used to dissolve these insecticides, but lesser amounts of a polar component, such as n-butanol or cyclohexanone are added to raise the viscosity and reduce the resistivity of the final formulations. The viscosity of these solutions is believed to be too high for effective delivery using a piezoelectric delivery system.

U.S. Pat. No. 5,935,554 is directed to an aerosol space spray which, in some embodiments, is an insecticidal composition. The composition includes an insecticide, a solvent and a propellant, and in some cases a co-solvent. Where an insecticide is used, the solvent is Shellsol T, with ethanol as a co-solvent.

European Patent No. 897,755 discloses aerosol and piezoelectric-deliverable insecticide compositions. Mentioned as solvents for the piezoelectric systems are aliphatic hydrocarbons, alicyclic hydrocarbons, aromatic hydrocarbons, halogenated hydrocarbons, alcohols, esters, ethers, and ketones, with a particular preference given to aliphatic saturated hydrocarbons having 5 to 18 carbon atoms. EP 897,755 does not identify polar solvents that would dissolve insecticides, nor does it identify the properties that render a polar solvent suitable for use with a piezoelectric delivery system.

Typical prior art liquid atomizers utilize a large amount of propellants in the formulation. Conventionally, to obtain the desired characteristics of an aerosol for dispersion into the air, the formulations contain minimal active ingredients, a solvent for the active ingredient and a suitable propellant. The active ingredient usually constitutes less than 1% w/w. The solvent is present in the order of 10–20% w/w and the propellant constitutes 80–90% w/w. In most cases of such aerosol formulations, the solvent is a hydrocarbon solvent and the propellant a fluorocarbon or hydrocarbon. Alternatively, the propellant is partially substituted with water, wherein the weight percentage being water is in the range of 30–40% w/w. Therefore it is evident that to deliver one gram of insecticide conventionally requires the release to the atmosphere of between 80 and 250 g of volatile organic compounds (VOC's). Volatile organic compound (VOC) is the general name given for compounds with an appreciable vapor pressure, for example, fluorocarbons, hydrocarbons, e.g. butane, etc., commonly used as propellants.

SUMMARY OF THE INVENTION

It is an object of the invention to provide an insecticidal composition which can be delivered with a piezoelectric delivery system. In particular, it is desired to provide an insecticidal composition with a sufficiently low viscosity that it can be delivered with a piezoelectric delivery system in the form of a fine mist or puff to provide continuous insect repellency throughout a room without settling too rapidly on surrounding surfaces.

Another object of the invention is to provide a low viscosity insecticidal composition that is not harmful or hazardous and which minimizes or eliminates the use of hydrocarbon solvents. In particular, it is desired to provide an insecticidal composition that exhibits overall low toxicity to humans and which will not be harmful to the respiratory system. It is also an object of the invention to provide an insecticidal composition that is non-flammable, and exhibits sufficiently low vapor pressure that latent losses are minimized when the formulation is used with a piezoelectric delivery device.

These and other objects of the invention are achieved by providing an insecticidal composition comprising an insecticide and at least one polar solvent having a vapor pressure below about 5 mm Hg at 25° C., where the insecticidal composition has a viscosity lower than 2.6 centipoise at 25° C. In preferred embodiments, the polar solvent comprises dipropylene glycol dimethyl ether.

Preferably, more than 75% of the solvent is a polar solvent or combination of polar solvents and co-solvents. In particularly preferred embodiments, the composition is substantially free of hydrocarbon solvents.

In preferred embodiments, the insecticidal composition according to the invention comprises an insecticide in an amount between about 3 percent by weight and about 20 percent by weight of the composition, while the solvent or solvents comprise between about 80 and 97 percent by weight of the composition.

The preferred formulations according to the invention are not emulsions and do not require propellants for delivery.

DETAILED DESCRIPTION OF THE PREFERRED EMBODIMENTS

As understood by those of skill in the art, a piezoelectric liquid atomizer comprises an orifice plate which is vibrated by an actuator made of a piezoelectric material, such as lead zirconate titanate (PZT) or lead metaniobate (PN). Upon application of an alternating electrical field across the piezoelectric actuator it expands and contracts and causes the orifice plate to vibrate. The vibrating orifice plate contacts a liquid and as a result liquid droplets are propelled ultrasonically through the orifices in the plate and ejected into the atmosphere.

The diameter of the orifices in the orifice plate of a piezoelectric liquid delivery system determines the size of the droplets produced. The diameter generally ranges between about 1 and about 25 microns, preferably from about 4 to about 10 microns. The size of the orifices is tailored such that energy consumption by the device is minimal while the size of the droplets is small enough to permit the droplets to remain suspended in the air and evaporate without collecting on the surrounding surfaces.

Droplets having an average size greater than about 15 to 20 microns and larger have a tendency to settle out of the air, onto the delivery device and other surfaces. Thus, it is advantageous to provide a solution that will produce droplets having a size less than 20 microns, preferably less than 15 microns. An average droplet size of about 10 microns has been observed to stay suspended in air for a suitable length of time to effectively kill insects in a room.

The low viscosity insecticidal compositions according to the invention are particularly suitable for piezoelectric delivery systems powered by low voltage batteries, such as conventional "A", "AA", "AAA", "C", "D" cell batteries and the like. In a particularly preferred embodiment, the insecticidal composition of the present invention is adapted for use with a piezoelectric delivery system powered by a single 1.5 Volt "AA" size battery.

Piezoelectric systems that may be used to deliver the insecticidal compositions of the present invention are disclosed in co-pending application Ser. Nos. 09/449,601, 09/498,859, 09/518,882, and 09/519,603, all of which are incorporated by reference herein in their entirety. However, the compositions described and claimed herein are not limited to those deliverable by the systems described in the above-referenced patent applications.

By way of description, without limiting the invention, the insecticidal composition may be delivered to a room via a piezoelectric delivery system at a rate between about 20 and about 40 mg/hour, with the insecticidally active component making up between about 3 and 20 percent of that amount.

It is generally preferred to obtain a delivery rate of about 1 to about 2 mg per hour of active insecticide so that a 10 ml bottle operated 8 hours a day will have a useful life between about 30 and about 70 days.

The use of a piezoelectric delivery device capable of prolonged delivery poses constraints on the solvent systems that can be used in insecticidal formulations. These constraints include: (1) the ability to solubilize insecticide, (2) low viscosity, (3) low vapor pressure, (4) high flash point, and (5) low toxicity (generally evidenced by high solubility in water).

"Solvent system" as used herein means the combination of all the solvents used in the insecticidal composition. "Main solvent" as used herein means a solvent comprising more than 50 percent by weight of the final formulation. "Co-solvent" means any solvent used in addition to the main solvent.

Generally, the active must be soluble in the solvent system of the formulation in an amount between about 2 percent by weight to about 10 percent by weight to be deliverable by a piezoelectric device.

It has been found that for the effective delivery of insecticide by a piezoelectric delivery system, low viscosity is critical. It is believed that a viscosity lower than 10 centipoise (cp) is necessary to obtain a suitable puff or mist using the preferred delivery systems according to the invention. The insecticidal compositions according to the invention preferably exhibit a viscosity of lower than about 2.6 cp, more preferably, lower than about 2.2 cp.

As the insecticides are generally high viscosity substances it is necessary to utilize a solvent system having a viscosity at least less than about 2.6 cp, and preferably less than 2.2 cp or lower, in the insecticidal formulations according to the invention.

In preparing the compositions of the present invention, the inventors have sought to lessen or eliminate the use of solvents which are harmful to inhale, such as those designated R20, R21 or R22; solvents irritating to the eyes or skin such as those designated R36 and R38; flammable solvents, such as those designated R10; and solvents harmful to the respiratory system when ingested, vomited and subsequently aspirated into the lungs, such as those designated R65. In general, it is desired that solvents having designation R20, R21 or R22 not exceed 25% by weight of the final formula; solvents having designation R36, R38 not exceed 20% of the final formula; and solvents having designation R65 not exceed 10% of the final formula. The R10 designation refers to low-flashpoint materials. It is desired that the formulations according to the invention have less than 20% by weight of solvents designated R10.

As used herein, a "low toxicity" composition is one containing less than 25 weight percent of R20, R21, or R22 solvents, less than 20 weight percent of R36 or R38 solvents, or less than 10 weight percent R65 solvent, and which has less than 25 weight percent hydrocarbon solvents overall. Limiting the use of solvents having the above-described hazard designations avoids conspicuous label designations, which is important in in formulating a commercially acceptable insecticidal product. Generally, polar solvents having high solubility in water are low-toxicity solvents.

The most preferred compositions according to the invention are substantially free of hydrocarbon solvents. "Substantially free" in this context allows for the presence of minor amounts of hydrocarbon solvents such as will not change the fundamental characteristics of the composition.

High solubility in water is a good indicator of low overall toxicity. Therefore, glycol ethers are good candidates to use as solvents or co-solvents in connection with the invention. For example, propylene glycol ethyl ether, propylene glycol n-propyl ether, ethylene glycol ethyl ether, and ethylene glycol propyl ether all have viscosities below 2.6 centipoise at 25° C., good solubility in water, and vapor pressure below 5 mm Hg at 20° C. Propylene glycol methyl ether has good water solubility and low viscosity; although its high vapor pressure (8.1 mm Hg at 20° C.) precludes its use as a main solvent, it can be used as a co-solvent. Ethylene glycol butyl ether, dipropylene glycol methyl ether, dipropylene glycol n-propyl ether, dipropylene glycol t-butyl ether, and tripropylene glycol methyl ether can also be used, although the viscosities of these glycol ether solvents are all greater than 2.6 cp, which may limit their use somewhat.

Diethylene glycol methyl ether, diethylene glycol ethyl ether, diethylene glycol propyl ether, and diethylene glycol butyl ether are all water soluble, have low vapor pressures and high flash points. However, their viscosities at 25° C. range between 3.9 and 4.7 cp, which may limit their use in formulations according to the invention.

It is desirable to keep the flash point of the final formula higher than about 55° C. (131° F.), as measured by the Penske Martin Close Cup Method (ASTM D93), more preferably higher than about 60° C. (140° F.).

The inventors herein have found that a solvent having a vapor pressure less than about 5 mm Hg at 20° C. must be used to avoid unacceptable latent losses in an insecticidal formulation over an extended period of delivery. Hydrocarbon solvents commonly used in analogous environments, such as Isopar C, Isopar G, Isopar L, Isopar E, and the like, have all been found to lead to unacceptable latent losses.

Dipropylene glycol dimethyl ether (DMM) has been found to meet the constraints of low vapor pressure (0.55 mm Hg at 20° C.), low viscosity (1 cp at 25° C.), and high water solubility as an indicator of low toxicity (35 g/100 ml water). Alone among the glycol ether solvents having these characteristics, DMM has a relatively high flash point (149° F. (65° C.)). Thus, in the preferred embodiments, DMM is the main solvent, used with one or more co-solvents.

In preferred embodiments, the insecticidal composition includes a co-solvent. The function of co-solvents is to improve the efficacy of the final formulation while still enabling the formulation to meet the constraints of high flash point, low volatility, low viscosity and low toxicity (as evidenced by high solubility in water). Accordingly the cosolvents themselves may have lower flash points, higher volatility, higher viscosity and lower solubility than the main solvent and still be acceptable for use in the solvent system according to the invention. Isopar L solvent, a hydrocarbon with very little water solubility and having an R65 hazard designation, may be used as a co-solvent in amounts less than about 10 percent by weight. Propylene glycol methyl ether acetate, which has a flash point of 114° F. and also carries an R36 hazard designation may be used as a co-solvent in amounts less than about 20 percent by weight with respect to the final formulation. Propylene glycol n-propyl ether (PnP), which has a flash point of 119° F. may be used as a co-solvent in amounts up to about 20 percent by weight. A preferred co-solvent is the cyclic amide N-methylpyrrolidone (NMP) used in amounts less than about 20 percent by weight.

The insecticides usable in the composition according to the invention are not particularly limited and include, without limitation, pyrethroid insecticides such as pyrethrin, allethrin, tetramethrin, resmethrin, etc.; organic phosphorus insecticides such as fenitrothion, ciafos, diazinon, etc.; carbamate insecticides such as carbaryl. The synthetic pyrethroids transfluthrin ((IR-trans)-2,3,5,6-tetraflurophenyl) methyl 3-(2,2-dichloroethyenyl)-2,3-dimethylcyclopropane carboxylate, a synthetic pyrethroid), and prallethrin ((RS)-2-Methyl-4-Oxo-3-(2-Propynyl) Cyclopent-2-enyl (1RS)-cis, transchrysanthemate), sometimes referred to as Etoc, are particularly preferred. Teflutlrin, pynamin, pynamin forte, and natural pyrethrum are all acceptable for use.

In some of the following examples, Pyrethrum 20 is used as an insecticide. Pyrethrum 20, available from Waxdale, is a mixture of pyrethrins in petroleum distillates and vegetable extracts, having 20 percent by weight active ingredients.

The following are examples according to the invention.

EXAMPLE 1

| | | |
|---|---|---|
| Insecticide | Prallethrin | 6 wt % |
| Solvent | DMM | 94 wt % |
| | Total | 100% |
| Composition Viscosity | | 1.104 cp |
| % Knockdown at 60/120 minutes | | 2/63 |

EXAMPLE 2

| | | |
|---|---|---|
| Insecticide | Prallethrin | 6 wt % |
| Solvent | PnP | 75 wt % |
| Co-solvent | PMA | 19 wt % |
| | Total | 100% |
| Composition Viscosity | | 2.259 cp |
| % Knockdown at 61/120 minutes | | 28/100 |

EXAMPLE 3

| | | |
|---|---|---|
| Insecticide | Prallethrin | 6 wt % |
| Solvent | PnP | 47 wt % |
| Co-solvent | DMM | 47 wt % |
| | Total | 100% |
| Composition Viscosity | | 1.599 cp |
| % Knockdown at 60/120 minutes | | 87/89 |

EXAMPLE 4

| | | |
|---|---|---|
| Insecticide | Prallethrin | 6 wt % |
| Solvent | DMM | 75 wt % |
| Co-solvent | NMP | 19 wt % |
| | Total | 100% |
| Composition Viscosity | | 2.259 cp |
| % Knockdown at 60/120 Minutes | | 100/100 |

EXAMPLE 5

| | | |
|---|---|---|
| Insecticide | Prallethrin | 6 wt % |
| Solvent | DMM | 85 wt % |
| Co-solvent | Isopar L | 9 wt % |
| | Total | 100% |
| Composition Viscosity | | 1.098 cp |
| % Knockdown at 60/120 Minutes | | 91/100 |

EXAMPLE 6

| | | |
|---|---|---|
| Insecticide | Prallethrin | 6 wt % |
| Solvent | DMM | 66 wt % |

-continued

| | | |
|---|---|---|
| Co-solvent | NMP | 19 wt % |
| Co-solvent | Isopar L | 9 wt% |
| | Total | 100% |
| Composition Viscosity | | 1.098 cp |
| % Knockdown at 60/120 Minutes | | 100/100 |

EXAMPLE 7

| | | |
|---|---|---|
| Insecticide | Prallethrin | 6 wt % |
| Solvent | DMM | 75 wt % |
| Co-solvent | DPM | 19 wt % |
| | Total | 100% |
| Composition Viscosity | | 1.324 cp |
| % Knockdown at 60/120 Minutes | | 100/100 |

EXAMPLE 8

| | | |
|---|---|---|
| Insecticide | Prallethrin | 10 wt % |
| Solvent | DMM | 71.4 wt % |
| Co-solvent | NMP | 18.6 wt % |
| | Total | 100 % |
| Composition Viscosity | | 1.638 cp |
| % Knockdown at 60/120 Minutes | | 100/100 |

EXAMPLE 9

| | | |
|---|---|---|
| Insecticide | Prallethrin | 15 wt % |
| Solvent | DMM | 67.4 wt % |
| Co-solvent | NMP | 17.6 wt % |
| | Total | 100 wt % |
| Composition Viscosity | | 1.723 cp |
| % Knockdown at 60/120 minutes | | 50/68 |

EXAMPLE 10

| | | |
|---|---|---|
| Insecticide | Pyrethrum 20 | 60 wt % |
| Solvent | DMM | 31.7 wt % |
| Co-solvent | Isopar L | 8.3 wt% |
| Composition | Total | 100% |
| Composition Viscosity | | 2.364 cp |
| % Knockdown at 60/120 minutes | | 100/100 |

EXAMPLE 11

| | | |
|---|---|---|
| Insecticide | Pyrethrum 20 | 40 wt % |
| Solvent | DMM | 47.8 wt % |
| Co-solvent | NMP | 12.2 wt % |
| | Total | 100% |
| Composition Viscosity | | 1.744 cp |
| % Knockdown at 60/120 minutes | | 72/100 |

EXAMPLE 12

| | | |
|---|---|---|
| Insecticide | Trans-fluthrin | 6 wt % |
| Solvent | DMM | 74.5 wt % |
| Co-solvent | Isopar L | 19.5 wt % |
| | Total | 100% |
| Composition Viscosity | | 1.441 cp |
| % Knockdown at 60/120 minutes | | 17/98 |

Viscosity measurements of the compositions in the above examples were obtained in a Bohlin Rheometer.

"Knockdown" refers to mosquitoes knocked down according to a test performed as follows. To obtain the percent knockdown data listed in the right hand column in the above Examples, piezoelectric atomizing units were placed on a 0.71 m (28 inch) stand in a 20 cubic meter chamber. The units were the designed to deliver a target amount of 2.00 mg active ingredient per hour, with actual amounts ranging between about 1.5 and about 3.5 mg active ingredient per hour of active ingredient.

Cylindrical cardboard cages with a volume of 240 ml, each containing approximately ten 14-day old Aedes aegypti mosquitoes were placed about 36 inches (0.91 m) from the center on each side of the cage and at three different heights (0.91, 1.37 and 1.84 meters). The number of mosquitoes knocked down at different intervals was recorded. The percentage of mosquitoes knocked down at one hour and at two hours is reported in the right hand column of the Example tables.

As demonstrated in these Examples, solvent systems containing a substantial amount of glycol ethers have been shown to produce surprisingly homogenous, low viscosity, and low toxicity solutions of common insecticides suitable for use with piezoelectric delivery systems.

What is claimed is:

1. An insecticidal composition consisting essentially of:
   an insecticide, and
   glycol ether solvent having viscosity lower than 2.6 centipoise at 20° C. and a vapor pressure below about 5 mm Hg at 20° C., and
   a co-solvent wherein said insecticidal composition has a viscosity lower than 2.6 centipoise at 20° C.

2. The insecticidal composition of claim 1, wherein said insecticidal composition has a viscosity less than about 2.2 centipoise at 20° C.

3. The insecticidal composition of claim 1, wherein said insecticidal composition has a flashpoint greater than about 60° C. as determined by the Penske Martin Closed Cup Method.

4. The insecticidal composition of claim 1, wherein said glycol ether is dipropylene glycol dimethyl ether.

5. The insecticidal composition of claim 1, wherein at least one co-solvent comprises N-methylpyrrolidone.

6. The insecticidal composition of claim 1, wherein said co-solvent is selected from the group consisting of hydrocarbon solvents NMP and DMM and mixtures thereof in an amount less than 25% by wt. of the composition.

7. The insecticidal composition of claim 1, substantially free of hydrocarbon solvents.

8. The insecticidal composition of claim 1, wherein the insecticide is present in an amount between about 3 to about 20 weight percent of said insecticidal composition.

9. The insecticidal composition of claim 1, wherein said insecticide contains at least one of transfluthrin, tefluthrin, pynamin, pynamin forte, natural pyrethrum, or prallethrin.

10. The insecticidal composition of claim 1, administered by piezoelectric dispenser.

11. The insecticidal composition of claim 1, wherein said composition is not an emulsion.

12. A low toxicity, non-emulsion, insecticidal composition consisting essentially of:
   between 3 weight percent to about 20 weight percent of a non-polar insecticide, and
   between about 80 weight percent to about 97 weight percent of a polar solvent,
   said polar solvent comprising at least one glycol ether having vapor pressure below about 5 mm Hg at 20° C., and
   said insecticidal composition having a viscosity lower than 2.6 cp at 20° C.

13. The insecticidal composition of claim 12, wherein said polar solvent comprises between about 60 to about 95 weight percent of a glycol ether and between about 2 to about 20 weight percent of a cyclic amide.

14. A low toxicity, non-emulsion insecticidal composition comprising:
   between about 3 weight percent to about 20 weight percent of a non-polar insecticide, about 5 to about 15 weight percent of the composition being prallethrin,
   between about 80 weight percent to about 97 weight percent of a polar solvent, about 65 to about 85 weight percent of the composition being dipropylene glycol dimethyl ether, and
   about 5 to about 20 weight percent of the composition being n-methylpyrrolidone,
   said insecticidal composition having a viscosity lower than 2.6 cp at 20° C.

* * * * *

UNITED STATES PATENT AND TRADEMARK OFFICE
CERTIFICATE OF CORRECTION

PATENT NO. : 6,482,863 B2
DATED : November 19, 2002
INVENTOR(S) : Murthy S. Munagavalasa, Gopal P. Ananth and Kevan Gartland It is certified that error appears in the above-identified patent and that said Letters Patent is hereby corrected as shown below:

Column 8,
Lines 66-67, delete "at least once"
Line 67, replace "comprises" with -- is --

Column 9,
Line 6, delete "substantially"

Column 10,
Line 7, replace "comprises" with -- ranges --

Signed and Sealed this

Fourth Day of January, 2005

JON W. DUDAS
*Director of the United States Patent and Trademark Office*